(12) United States Patent
Mathis (10) Patent No.: US 6,562,067 B2
(45) Date of Patent: May 13, 2003

(54) STENT WITH INTERLOCKING ELEMENTS (75) Inventor: Mark Mathis, Kirkland, WA (US)

(73) Assignee: Cordis Corporation, Miami Lakes, FL (US)

(*) Notice: Subject to any disclaimer, the term of this patent is extended or adjusted under 35 U.S.C. 154(b) by 1 day.

(21) Appl. No.: 09/877,506

(22) Filed: Jun. 8, 2001

(65) Prior Publication Data

US 2002/0188347 A1 Dec. 12, 2002

(51) Int. Cl.7 .................................................. A61F 2/06
(52) U.S. Cl. ........................ 623/1.16; 623/1.2; 606/198; 606/195
(58) Field of Search ............................. 623/1.16, 1.15, 623/1.17, 1.18, 1.2, 1.21, 1.22; 606/191, 195, 198, 194

(56) References Cited

U.S. PATENT DOCUMENTS

| 5,041,126 | A | * | 8/1991 | Gianturco | 604/104 |
| 5,824,059 | A | * | 10/1998 | Wijay | 623/1.15 |
| 5,879,370 | A | * | 3/1999 | Fischell et al. | 606/198 |
| 5,879,381 | A | * | 3/1999 | Moriuchi et al. | 606/195 |
| 5,911,754 | A | * | 6/1999 | Kanesaka et al. | 606/198 |
| 6,017,365 | A | * | 1/2000 | Von Oepen | 623/1.15 |
| 6,340,366 | B2 | * | 1/2002 | Wijay | 623/1.13 |
| 6,344,053 | B1 | * | 2/2002 | Boneau | 606/198 |
| 6,375,676 | B1 | * | 4/2002 | Cox | 606/196 |
| 6,375,677 | B1 | * | 4/2002 | Penn et al. | 623/1.15 |
| 6,416,539 | B1 | * | 7/2002 | Hassdenteufel | 623/1.15 |
| 2002/0111671 | A1 | | 8/2002 | Stenzel | |

* cited by examiner

Primary Examiner—Danny Worrell
(74) Attorney, Agent, or Firm—Louis J. Capezzuto (57) ABSTRACT A stent comprises a lattice of interconnecting elements defining a substantially cylindrical configuration having a first open end and a second open end. The lattice has a locked configuration and an open configuration. The stent also comprises a plurality of bridges connecting the interconnecting elements wherein each bridge interlocks with an adjacent bridge in the locked configuration and each bridge separates from the adjacent bridge in the open configuration. A second embodiment for the stent also comprises a lattice of interconnecting elements including a plurality of struts wherein each strut interlocks with an adjacent strut in the locked configuration and each strut separates from the adjacent strut in the open configuration.

36 Claims, 10 Drawing Sheets

FIG. 4B

STENT WITH INTERLOCKING ELEMENTS

FIELD OF THE INVENTION

The present invention relates, in general, to intraluminal medical devices, and, more particularly, two a new and useful stent, stent delivery apparatus and method for stenting a vessel using a stent with interlocking elements.

BACKGROUND ART

A stent is commonly used as a tubular structure left inside the lumen of a duct to relieve an obstruction. Commonly, stents are inserted into the lumen in a non-expanded form and are then expanded autonomously (or with the aid of a second device) in situ. When used in coronary artery procedures for relieving stenosis, stents are placed percutaneously through the femoral artery. In this type of procedure, stents are delivered on a catheter and are either self-expanding or, in the majority of cases, expanded by a balloon. Self-explanding stents do not need a balloon to be deployed. Rather the stents are constructed using metals with spring-like or superelastic properties (i.e., Nitinol), which inherently exhibit constant radial support. Self-expanding stents are also often used in vessels close to the skin (i.e., carotid arteries) or vessels that can experience a lot of movement (i.e., popliteal artery). Due to a natural elastic recoil, self-expanding stents withstand pressure or shifting and maintain their shape.

As mentioned above, the typical method of expansion for balloon expanded stents occurs through the use of a catheter mounted angioplasty balloon, which is inflated within the stenosed vessel or body passageway, in order to shear and disrupt the obstructions associated with the wall components of the vessel and to obtain an enlarged lumen.

Balloon-expandable stents involve crimping the device onto an angioplasty balloon. The stent takes shape as the balloon is inflated and remains in place when the balloon and delivery system are deflated and removed.

In addition, balloon-expandable stents are available either pre-mounted or unmounted. A pre-mounted system has the stent already crimped on a balloon, while an unmounted system gives the physician the option as to what combination of devices (catheters and stents) to use. Accordingly, for these types of procedures, the stent is first introduced into the blood vessel on a balloon catheter. Then, the balloon is inflated causing the stent to expand and press against the vessel wall. After expanding the stent, the balloon is deflated and withdrawn from the vessel together with the catheter. Once the balloon is withdrawn, the stent stays in place permanently, holding the vessel open and improving the flow of blood.

In the absence of a stent, restenosis may occur as a result of elastic recoil of the stenotic lesion. Although a number of stent designs have been reported, these designs have suffered from a number of limitations. Some of these limitations include premature deployment of the stent due to circumstances such as over-manipulation when traversing tortuous vessels or the inability to maintain the stent secured to the balloon due to migration, slippage, etc.

Accordingly, to date, there have not been any stent designs, that specifically address these drawbacks in an efficient and cost effective manner.

BRIEF SUMMARY OF THE INVENTION

The present invention relates to an apparatus and method for stenting a vessel in conjunction with a particular new and useful stent having a lattice of interconnecting elements defining a substantially cylindrical configuration. The lattice has a first open end and a second open end wherein the lattice is movable between a locked configuration and an open configuration.

One embodiment of the stent includes a plurality of bridges connecting the interconnecting elements wherein each bridge interlocks with an adjacent bridge in the locked configuration and wherein each bridge separates from the adjacent bridge in the open configuration.

In another embodiment, the interlocking elements include a plurality of struts wherein each strut interlocks with an adjacent strut in the locked configuration and each strut separates from the adjacent strut in the open configuration.

For the interlocking bridge embodiment, each bridge has a projection and a base wherein the base has a projection holding section for receiving the projection from an adjacent bridge. Likewise, for the interlocking strut embodiment, each strut has a projection and a base wherein the base has a projection holding section for receiving the projection from an adjacent strut. Accordingly, for both of the stent embodiments identified above, several features are in common. For instance, the interlocking elements comprise a plurality of adjacent sections. Additionally, the adjacent sections comprise adjacent hoops wherein each hoop comprises a plurality of loops. Each loop comprises at least one strut.

For both the interlocking bridge embodiment and the interlocking strut embodiment, lateral arms extend from the base. Moreover, the projection holding section of the base has an opening therein for receiving the projection. An extension is connected between the base and the projection, and, for the interlocking bridge embodiment, the extension includes a neck wherein the projection is located at a superior position on the neck.

The projection also includes at least one lateral lip and the projection holding section includes at least one lateral ledge for releasably engaging the at least one lateral lip of the projection. The projection also includes at least one sidewall adjacent to the at least one lateral lip. Additionally, the projection holding section includes at least one lateral depression adjacent to the at least one lateral ledge for releasably engaging the at least one sidewall of the projection.

Although these features are intended to encompass any suitable configuration, in a preferred embodiment, the at least one sidewall is curved and the at least one depression is curved wherein these elements are aligned, snapped-fit or interlock in a puzzle-lock manner. Moreover, the lateral arms of the base connect directly to the interconnecting elements of the lattice.

The stent of the present invention is directed toward both a balloon actuated stent and a self-expanding stent. The stent is made of any suitable material. In one embodiment, the stent is made of an alloy such as stainless steel. In another preferred embodiment, the stent is made of a nickel titanium (Nitinol) alloy. Moreover, this material or any other superelastic alloy is suitable for the stent according to the present invention. In these self-expanding stent embodiments, the stent is a crush recoverable stent.

The present invention is also directed toward an apparatus and method for stenting a vessel utilizing the stent embodiments described above, e.g., a stent having a lattice of interconnecting elements and including interlocking features such as a plurality of interlocking bridges in one embodiment or a plurality of interlocking struts in another embodiment.

The apparatus further includes a catheter having an inner sleeve and an expandable member on the inner sleeve wherein the expandable member is movable between a collapsed state and an expanded state. One of the stent embodiments described above is secured to the catheter over the expandable member when the expandable member is in the collapsed state and the stent is in the locked configuration. The stent is separated or deployed from the catheter when the expandable member is in the expanded state and the stent is in the open configuration. The apparatus further includes a cover movably disposed over the stent. The cover is an outer sheath made of a polymer material. Additionally, the expandable member is an inflatable balloon.

The method for stenting a vessel according to the present invention comprises the steps of providing the apparatus according to the present invention have one of the stent embodiments, e.g., the interlocking bridge embodiment or the interlocking strut embodiment, and inserting the apparatus within a vessel. The distal end of the apparatus is positioned at a desired location within the vessel and the stent is deployed to the open configuration with the expandable member.

Additionally, the method further includes providing the cover movably disposed over the stent for preventing the stent from moving to the open configuration until desired. The method further comprises deploying the stent to the open configuration by inflation of the expandable member.

Additionally, the method further comprises securing the stent to the catheter by interlocking the bridges (for the interlocking bridge embodiment) or by interlocking the struts (for the interlocking strut embodiment) prior to performing certain steps according to the present invention. Lastly, the method according to the present invention also comprises removing the catheter from the patient after the deployment of the stent.

BRIEF DESCRIPTION OF THE DRAWINGS

The novel features of the invention are set forth with particularity in the appended claims. The invention itself, however, both as to organization and methods of operation, together with further objects and advantages thereof, may be best understood by reference to the following description, taken in conjunction with the accompanying drawings in which:

DETAILED DESCRIPTION OF THE INVENTION

In FIGS. 1A, 1B, 4A and 4B, a stent 100 that is an expandable prosthesis for a body passageway is illustrated. It should be understood that the terms "stent" and "prosthesis" are interchangeably used to some extent in describing the present invention, insofar as the method, apparatus, and structures of the present invention may be utilized not only in connection with an expandable intraluminal vascular graft for expanding partially occluded segments of a blood vessel, duct or body passageways, such as within an organ, but may so be utilized for many other purposes as an expandable prosthesis for many other types of body passageways. For example, expandable prostheses may also be used for such purposes as: (1) supportive graft placement within blocked arteries opened by transluminal recanalization, but which are likely to collapse in the absence of internal support; (2) similar use following catheter passage through mediastinal and other veins occluded by inoperable cancers; (3) reinforcement of catheter created intrahepatic communications between portal and hepatic veins in patients suffering from portal hypertension; (4) supportive graft placement of narrowing of the esophagus, the intestine, the ureters, the uretha, etc.; (5) intraluminally bypassing a defect such as an aneurysm or blockage within a vessel or organ; and (6) supportive graft reinforcement of reopened and previously obstructed bile ducts. Accordingly, use of the term "prothesis" encompasses the foregoing usages within various types of body passageways, and the use of the term "intraluminal graft" encompasses use for expanding the lumen of a body passageway. Further in this regard, the term "body passageway" encompasses any lumen or duct within the human body, such as those previously described, as well as any vein, artery, or blood vessel within the human vascular system.

The stent 100 is an expandable lattice structure made of any suitable material which is compatible with the human body and the bodily fluids (not shown) with which the stent 100 may come into contact. The lattice structure is an arrangement of interconnecting elements made of a material which has the requisite strength and elasticity characteristics to permit the tubular shaped stent 100 to be expanded from the closed configuration shown in FIGS. 1A and 1B to the expanded configuration shown in FIGS. 4A and 4B and further to permit the stent 100 to retain its expanded configuration at the enlarged diameter $d_1$. Suitable materials for the fabrication of the stent 100 include silver, tantalum, stainless steel, gold, titanium or any suitable plastic material having the requisite characteristics previously described. In one embodiment, the stent is fabricated from 316L stainless steel alloy In a preferred embodiment, the stent 100 comprises a superelastic alloy such as nickel titanium (NiTi, e.g., Nitinol). More preferably, the stent 100 is formed from an alloy comprising from about 50.5 to 60.0% Ni by atomic weight and the remainder Ti. Even more preferably, the stent 100 is formed from an alloy comprising about 55% Ni and about 45% Ti. The stent 100 is preferably designed such that it is superelastic at body temperature, and preferably has an Af temperature in the range from about 24° C. to about 37° C. The superelastic design of the stent 100 makes it crush recoverable and thus suitable as a stent or frame for any number of vascular devices for different applications.

Figure 4A:
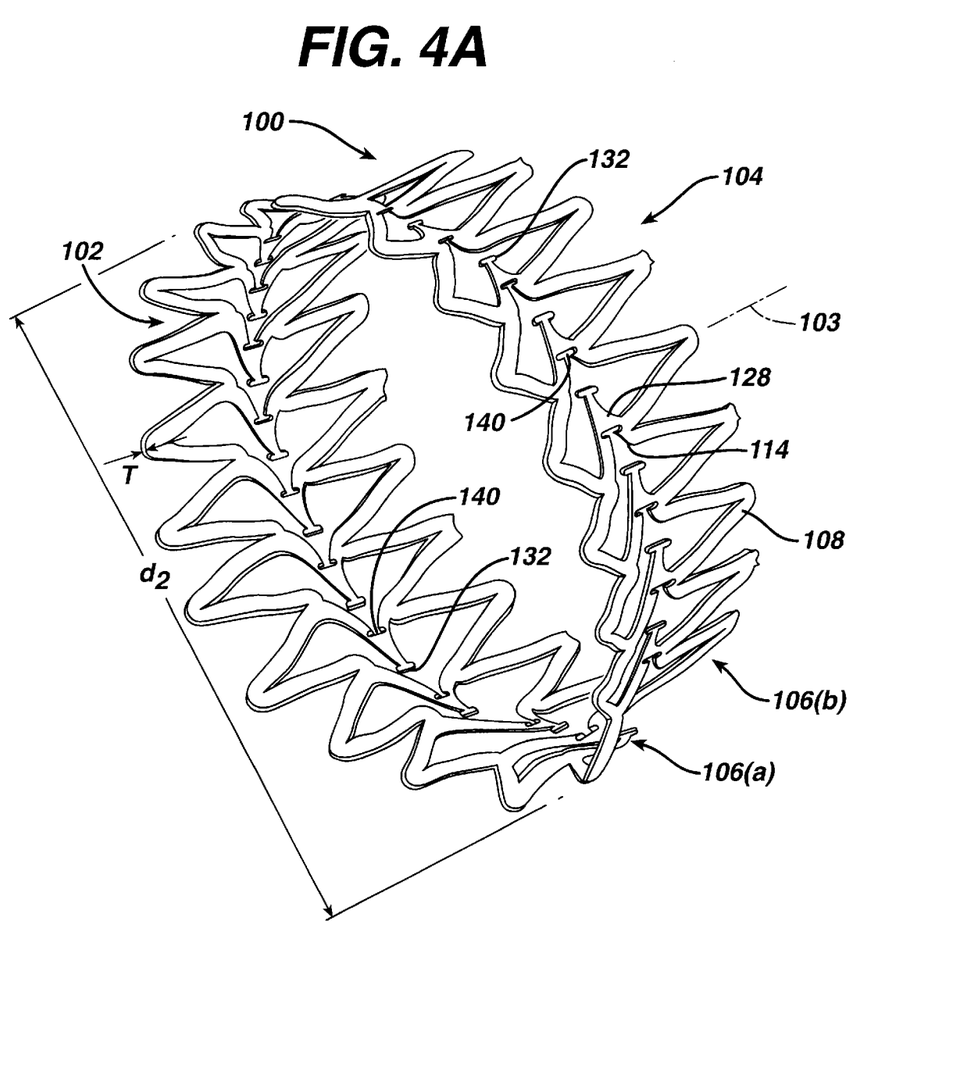
FIG. 4A is a partial perspective view of the stent of FIG. 1A in an open configuration.
Figure 4B:
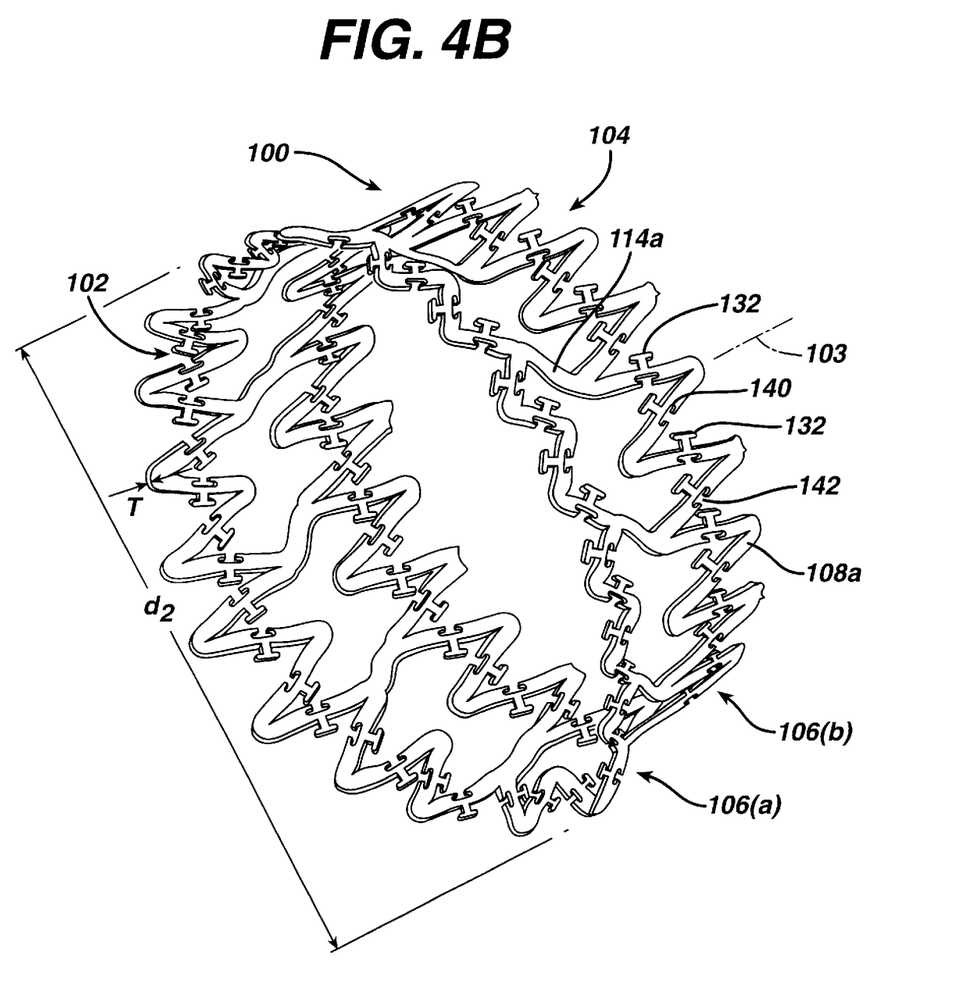
FIG. 4B is a partial perspective view of the stent of FIG. 1B in an open configuration.

The stent 100 comprises a tubular configuration formed by a lattice of interconnecting elements defining a substantially cylindrical configuration and having front and back open ends 102, 104 and defining a longitudinal axis 103 extending therebetween. In its closed configuration, the stent 100 has a first diameter ($d_1$) for insertion into a patient and navigation through the vessels and, in its open configuration, a second diameter ($d_2$), as shown in FIGS. 4A and 4B, for deployment into the target area of a vessel with the second diameter being greater than the first diameter. The stent 100 comprises a plurality of adjacent hoops 106(a)–(d) extending between the front and back ends 102, 104. The hoops 106(a)–(d) include a plurality of longitudinally arranged struts 108 and a plurality of loops 110 connecting adjacent struts 108. Adjacent struts 108 are connected at opposite ends so as to form a substantially S or Z shape pattern. The plurality of loops 110 have a substantially semi-circular configuration and are substantially symmetric about their centers.

Figure 2A:
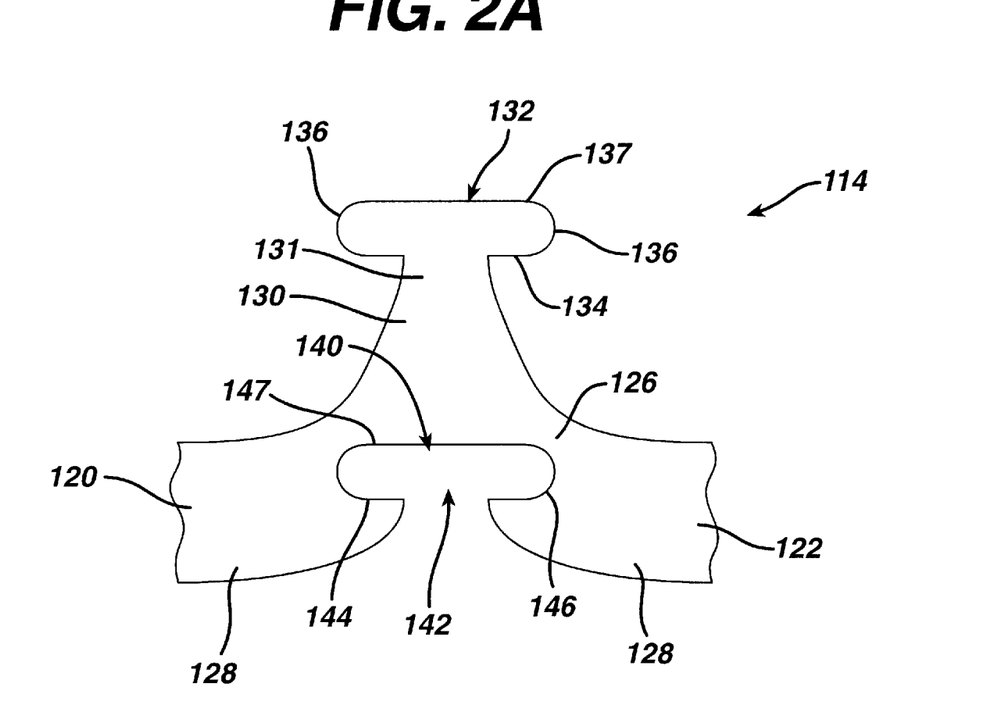
FIG. 2A is a partial side plan view of an interlocking bridge for the stent of FIG. 1A.

The stent 100 further comprises a plurality of bridges 114, which connect adjacent hoops 106(a)–(d). The details of the bridges 114 are more fully illustrated in FIGS. 2A, and 3A and described below. Each bridge comprises two ends wherein one end of each bridge 114 is attached to one loop 110 on one hoop 106(a) and the other end of each bridge 114 is attached to one loop 110 on an adjacent hoop 106(b). The bridges 114 connect adjacent hoops 106(a)–(d) together at bridge to loop connection regions 120,122 as shown in FIG. 2A.

The above-described geometry better distributes strain throughout the stent 100, prevents metal to metal contact where the stent 100 is bent, and minimizes the opening between the features of the stent 100; namely, struts 108, loops 110 and bridges 114. The number of and nature of the design of the struts, loops and bridges are important design factors when determining the working properties and fatigue life properties of the stent 100. It was previously thought that in order to improve the rigidity of the stent, struts should be large, and thus there should be fewer struts 108 per hoop 106(a)–(d). However, it is now known that stents 100 having smaller struts 108 and more struts 108 per hoop 106(a)–(d) improve the construction of the stent 100 and provide greater rigidity. Preferably, each hoop 106(a)–(d) has between twenty-four (24) to thirty-six (36) or more struts 108. It has been determined that a stent having a ratio of number of struts per hoop to strut length which is greater than four hundred has increased rigidity over prior art stents which typically have a ratio of under two hundred. The length of a strut is measured in its compressed state parallel to the longitudinal axis 103 of the stent 100 as illustrated in FIG. 1A.

FIG. 4A illustrates the stent 100 in its open or expanded state. As may be seen from a comparison between the stent 100 configuration illustrated in FIG. 1A and the stent 100 configuration illustrated in FIG. 4A, the geometry of the stent 100 changes quite significantly as it is deployed from its unexpanded state (closed or locked configuration) to its expanded state (open or unlocked configuration). As the stent 100 undergoes diametric change, the strut angle and strain levels in the loops 110 and bridges 114 are affected. Preferably, all of the stent features will strain in a predictable manner so that the stent 100 is reliable and uniform in strength. In addition, it is preferable to minimize the maximum strain experienced by the struts 108, loops 110 and bridges 114 since Nitinol properties are more generally limited by strain rather than by stress. The embodiments illustrated in FIGS. 1A–5B has a design to help minimize forces such as strain.

Figure 1A:
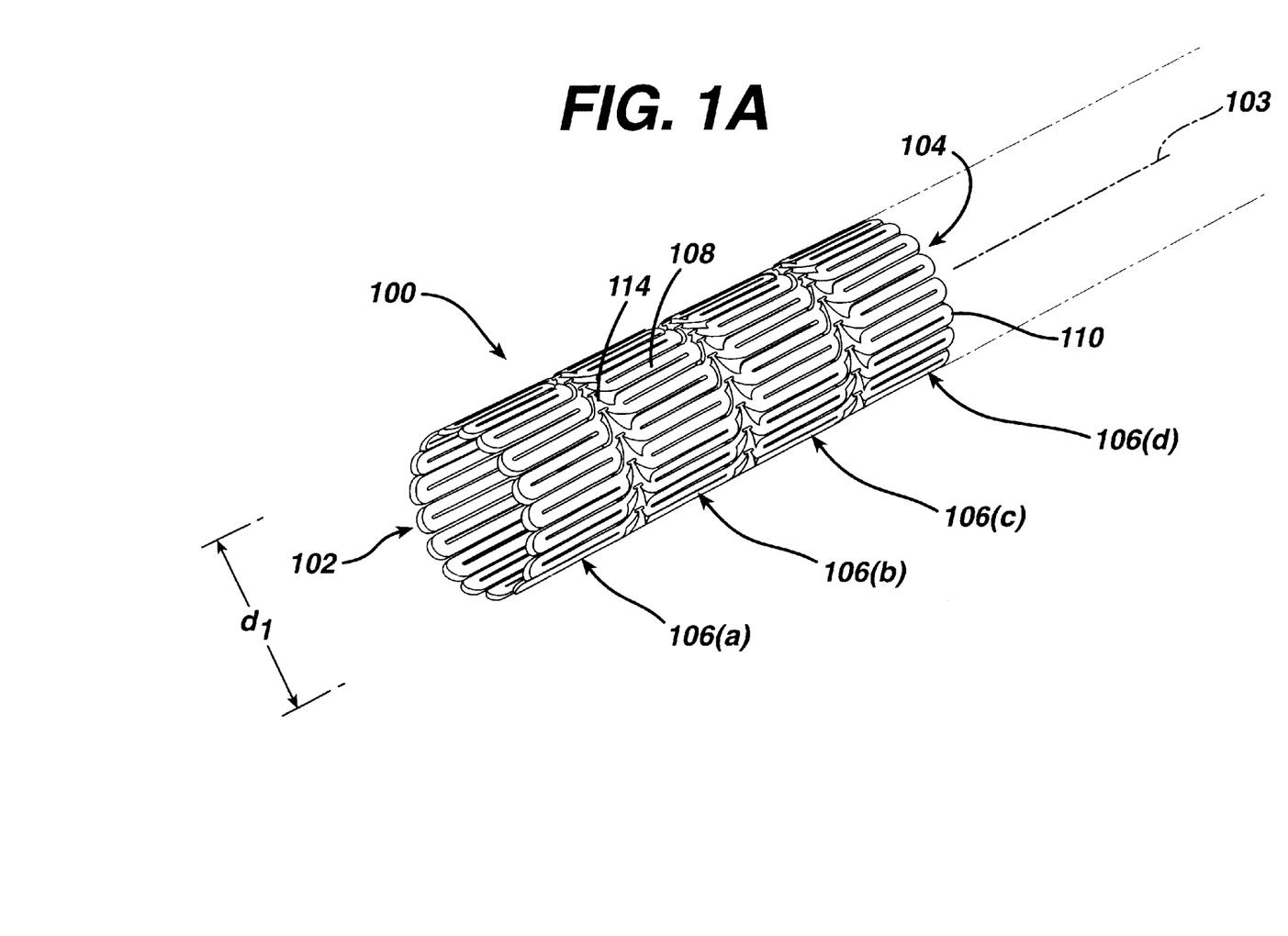
FIG. 1A is a perspective view of a first embodiment of a stent in a closed configuration in accordance with the present invention.

FIG. 1A illustrates the first embodiment of the stent 100 according to the present invention including a plurality of interlocking bridges 114 connecting adjacent hoops 106(a)–(d). In this embodiment, as best illustrated in FIG. 2A, stent 100 has bridges 114 wherein each bridge 114 includes a base 126. The base 126 has a pair of laterally extending arms 128 wherein each end of the lateral arms 128 are connected directly to a loop 110 at loop connection regions 120 and 122. Accordingly, one laterally extending arm connects to one of the adjacent hoops 106(a)–(d) at the loop connection region 120 of one loop 110 and the other lateral extending arm 128 of the bridge 114 is connected to an adjacent loop 110 at the loop connection region 122. Thus, the bridge 114 alternatively connects adjacent hoops 106(a)–(d).

The bridge 114 further includes an extension 130 extending in a superior direction from the base 126. The extension 130 includes a neck 131 at the superior end of the extension 130. A projection 132 is fixed to the superior end of the neck 131 of the extension 130. Although the projection 132 can comprise any desired configuration, one preferred configuration for the projection 132 includes a pair of lateral lips 134 laterally extending from the neck 131 and a pair of lateral sidewalls 136 extending from the lateral lips 134 respectively. In this embodiment, the lateral sidewalls 136 have a curved-shape. Additionally, the projection 132 further includes an upper edge 137 extending between the lateral sidewalls 136.

The bridge 114 further includes a projection holding section 140 inferior to the extension 130 at the base 126. The projection holding section 140 is defined by an opening 142 in the base 126. The projection holding section 140 further includes a pair of lateral ledges 144 extending from each side of the opening 142. The projection holding section 140 further includes a lateral depression 146 extending from each lateral ledge 144. Each lateral depression 146 also has a curved-shape for this embodiment. Additionally, the projection holding section 140 includes an upper edge 147 extending between each lateral depression 146.

The projection holding section 140 is shaped to fit and receive in a snap-fit or puzzle-lock manner the projection 132 of an adjacent bridge 114. Due to the unique configuration of the bridge 114, the projection 132 of a first bridge 114 is interlocked with the projection holding section 140 of a second bridge 114. The interlocking of bridges 114, which can be adjacent bridges, is accomplished by insertion of the projection 132 of the first bridge 114 into the central opening 142 of the projection holding section 140 of the second bridge 114 such that the lateral lips 134 releasably engage the lateral ledges 144 of the projection holding section 140. Moreover, the lateral sidewalls 136 of the projection 132 mates, in a releasable fashion, with the lateral depressions 146 of the projection holding section 140 of the second bridge 114. Furthermore, the upper edge 137 of the projection 132 of the first bridge 114 releasably mates with the upper edge 147 of the projection holding section 140 of the second bridge 114. Accordingly, this arrangement insures for an interlocking of the first and second bridges 114, e.g., adjacent bridges 114, in a puzzle-like manner. This arrangement of interlocking bridges 114 is clearly illustrated in FIG. 3A. When deployed to an open configuration, the stent 100 for the interlocking bridge embodiment described above expands to a width $D_2$ as shown in FIG. 4A.

Figure 1B:
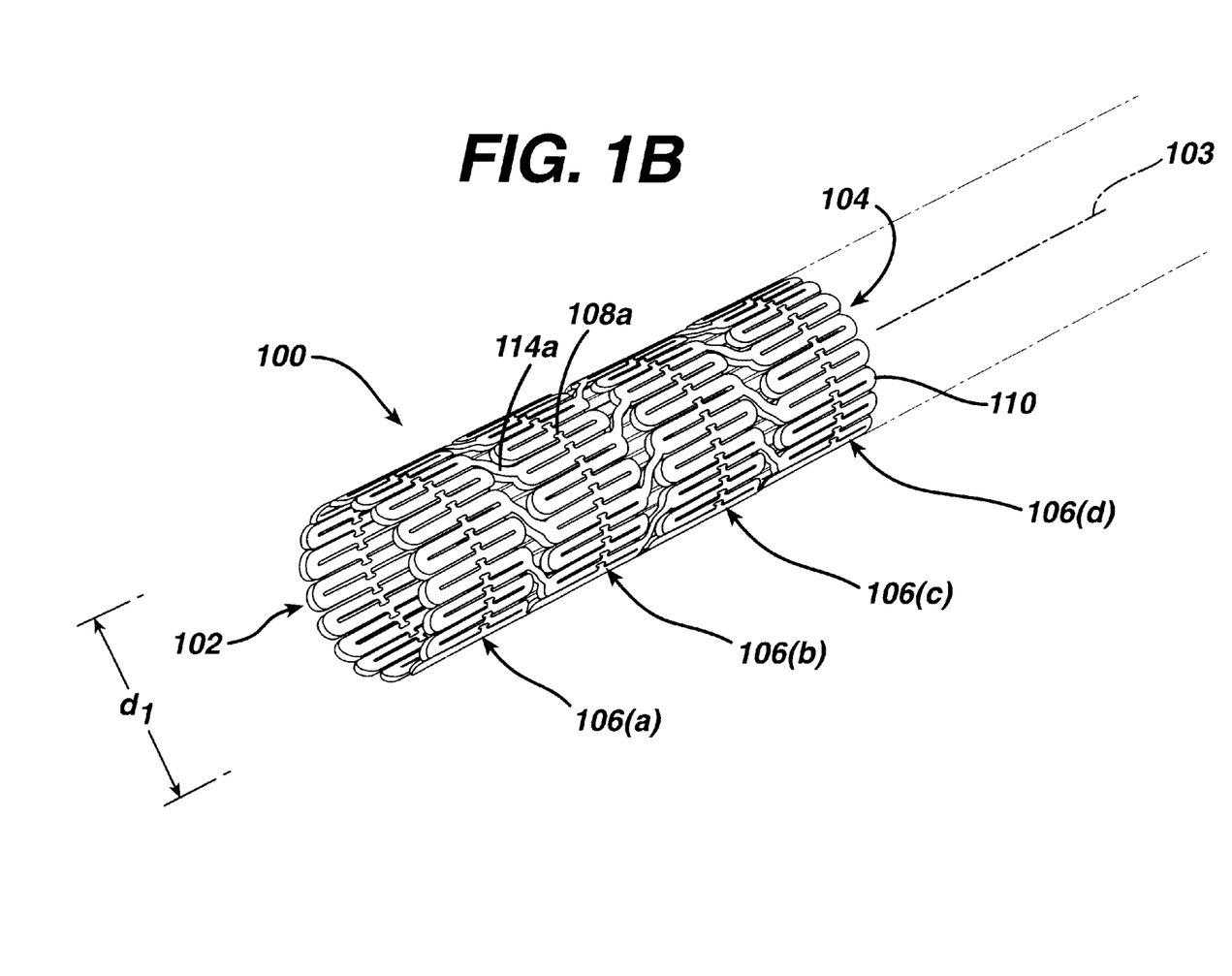
FIG. 1B is a perspective view of a second embodiment of a stent in a closed configuration in accordance with the present invention.

A second embodiment for the stent 100 is shown in FIG. 1B and includes a plurality of interlocking struts 108a. In this embodiment, adjacent hoops 106(a)–(d) are connected to each other by nonlocking bridges 114a.

Figure 3A:
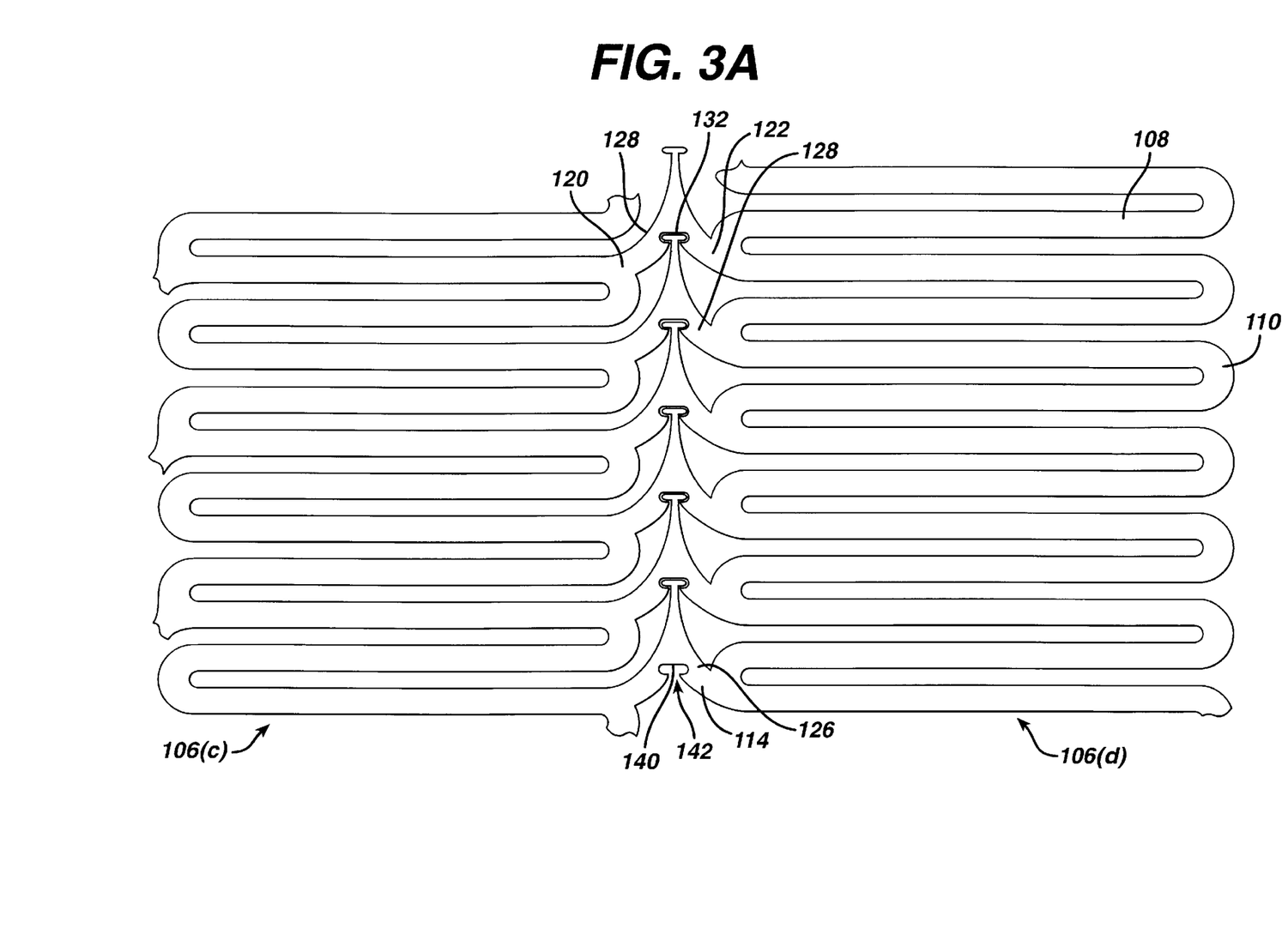
FIG. 3A is a partial side view of the lattice of the stent of FIG. 1A.
Figure 3B:
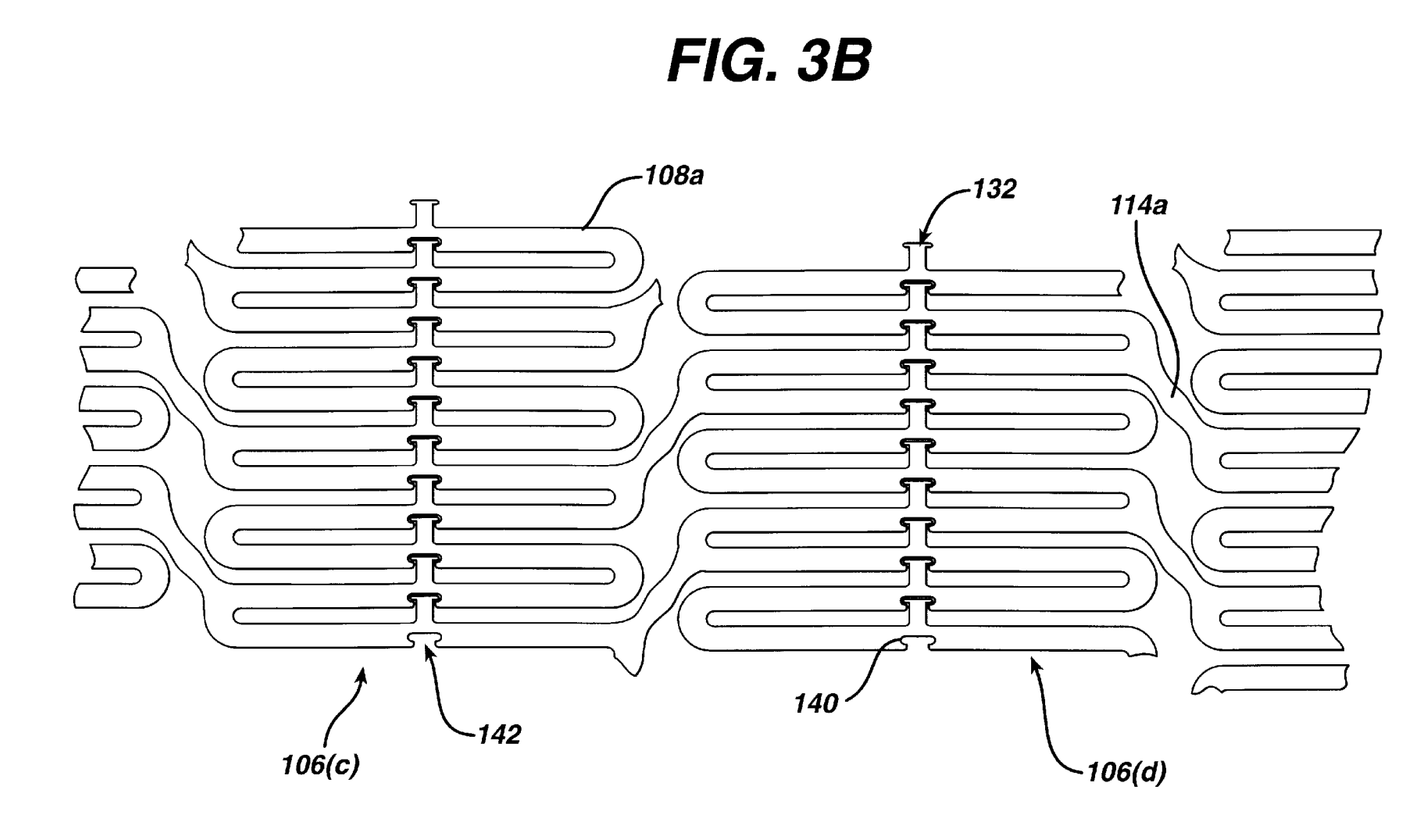
FIG. 3B is a partial side view of the lattice of the stent of FIG. 1B.

For the embodiment of FIG. 1B (the interlocking strut embodiment), a plurality of interlocking struts 108a are utilized in order to interlock by releasable engagement a first strut 108a with a second strut 108a as best shown in FIG. 3B.

For purposes of this disclosure, the same reference numerals are used to designate like or similar features for both the interlocking bridge 114 embodiment (FIG. 1A) and the interlocking strut 108a embodiment (FIG. 1B). Accordingly, each interlocking strut 108a includes base 126 and laterally extending sidearms 128 as shown in FIG. 2B.

Figure 2B:
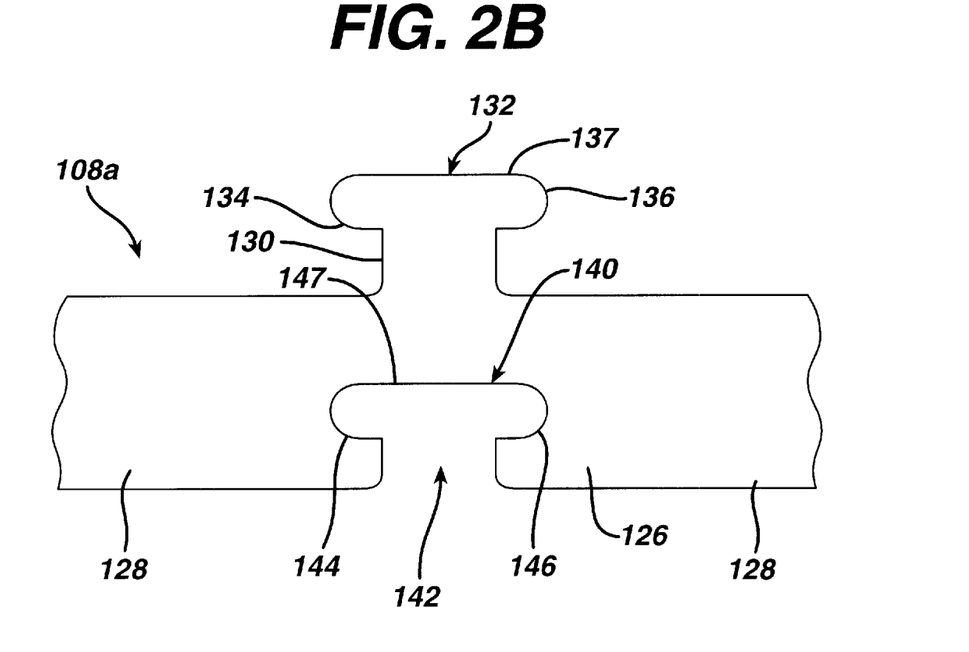
FIG. 2B is a partial side plan view of an interlocking strut for the stent of FIG. 1B.

As illustrated in FIG. 2B, the strut 108a further includes extension 130 extending in a superior direction from the base 126. Projection 132 is fixed to the superior end of the extension 130. Although the projection 132 can comprise any desired configuration, one preferred configuration for the projection 132 includes a pair of lateral lips 134 laterally extending from the extension 130 and a pair of lateral sidewalls 136 extending from the lateral lips 134 respectively. In this embodiment, the lateral sidewalls 136 have a curved-shape. Additionally, the projection 132 further includes upper edge 137 extending between the sidewalls 136.

The strut 108a (of the interlocking strut embodiment) further includes projection holding section 140 inferior to the extension 130 at the base 126. The projection holding section 140 is defined by opening 142 in the base 126. The projection holding section 140 further includes a pair of lateral ledges 144 extending from each side of the opening 142. The projection holding section 140 further includes lateral depression 146 extending from each lateral ledge 144. Each lateral depression 146 also has a curved-shape for this embodiment. Additionally, the projection holding section 140 includes upper edge 147 extending between each lateral depression 146.

As best illustrated in FIG. 3B, the projection holding section 140 is shaped to fit and receive in a snap-fit or puzzle-lock manner the projection 132 of an adjacent strut 108a. Due to the unique configuration of the strut 108a, the projection 132 of a first strut 108a is interlocked with the projection holding section 140 of a second strut 108a. The interlocking of struts 108a, which can be adjacent struts, is accomplished by insertion of the projection 132 of the first strut 108a into the central opening 142 of the projection holding section 140 of the second strut 108a such that the lateral lips 134 releasably engage the lateral ledges 144 of the projection holding section 140. Moreover, the lateral sidewalls 136 of the projection 132 mates, in a releasable fashion, with the lateral depressions 146 of the projection holding section 140 of the second strut 108a. Furthermore, the upper edge 137 of the projection 132 of the first strut 108a releasably mates with the upper edge 147 of the projection holding section 140 of the second strut 108a. Accordingly, this arrangement insures for an interlocking of the first and second struts 108a, e.g., adjacent struts 108a, in a puzzle-like manner. This arrangement of interlocking struts 108a is clearly illustrated in FIG. 3B. Thus, the first strut 108a releasably engages with or interlocks with the second strut 108a in a puzzle-lock manner.

As mentioned above with the interlocking bridge embodiment of FIG. 4A, as shown in FIG. 4B, the stent 100 having the interlocking struts 108a (the inerlocking strut embodiment) is deployed or expanded to an open configuration having a width $D_2$.

The stent 100 according to the present invention for both the interlocking bridge 114 embodiment and the interlocking strut 108a embodiment is directed toward both deployment or expansion through an expandable member such as a balloon (to be described in greater detail below) and a self-expanding stent, i.e., a stent that is crush recoverable.

Figure 5A:
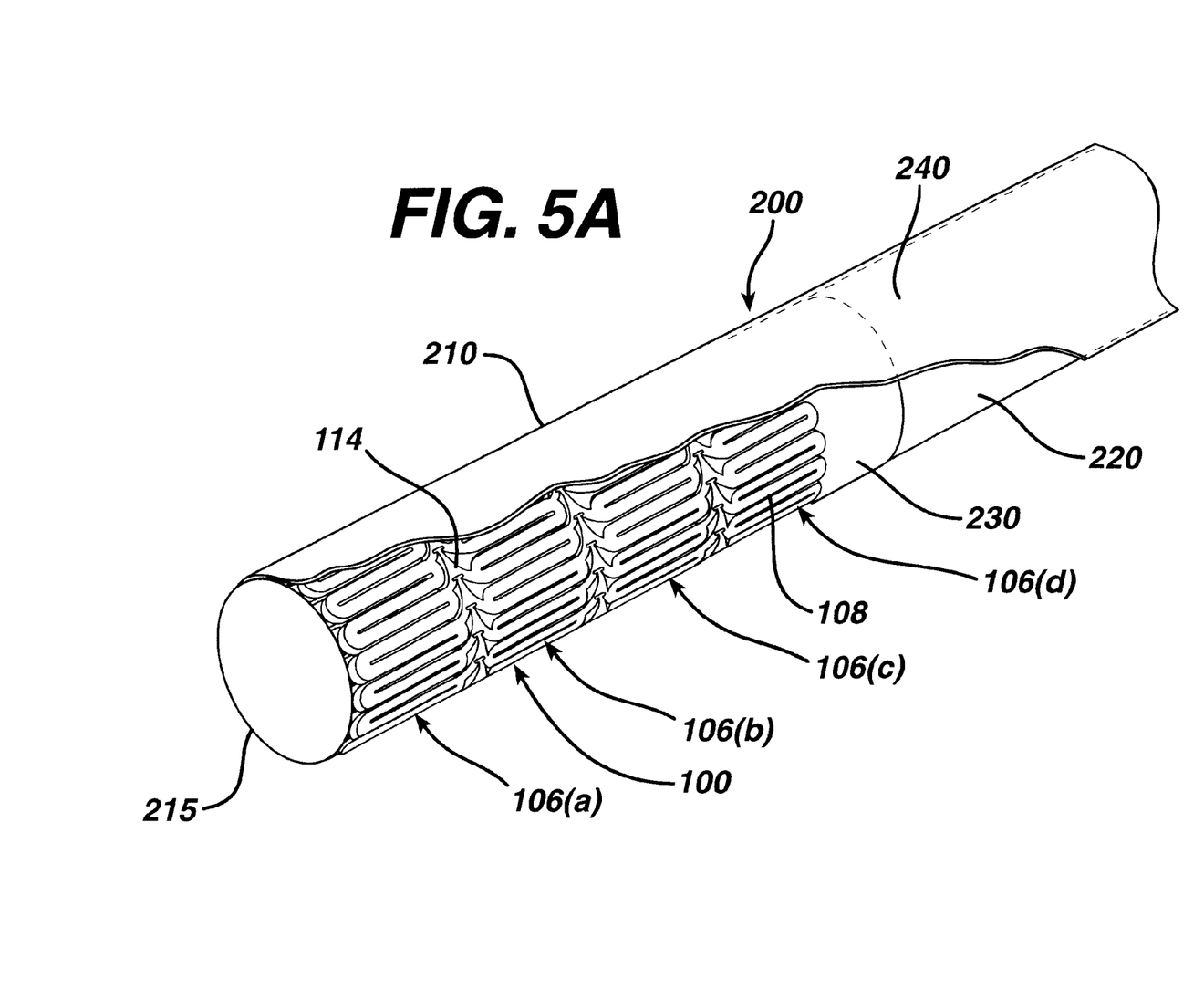
FIG. 5A is a partial perspective view of a distal end of an apparatus according to the present invention utilizing the stent of FIG. 1A.
Figure 5B:
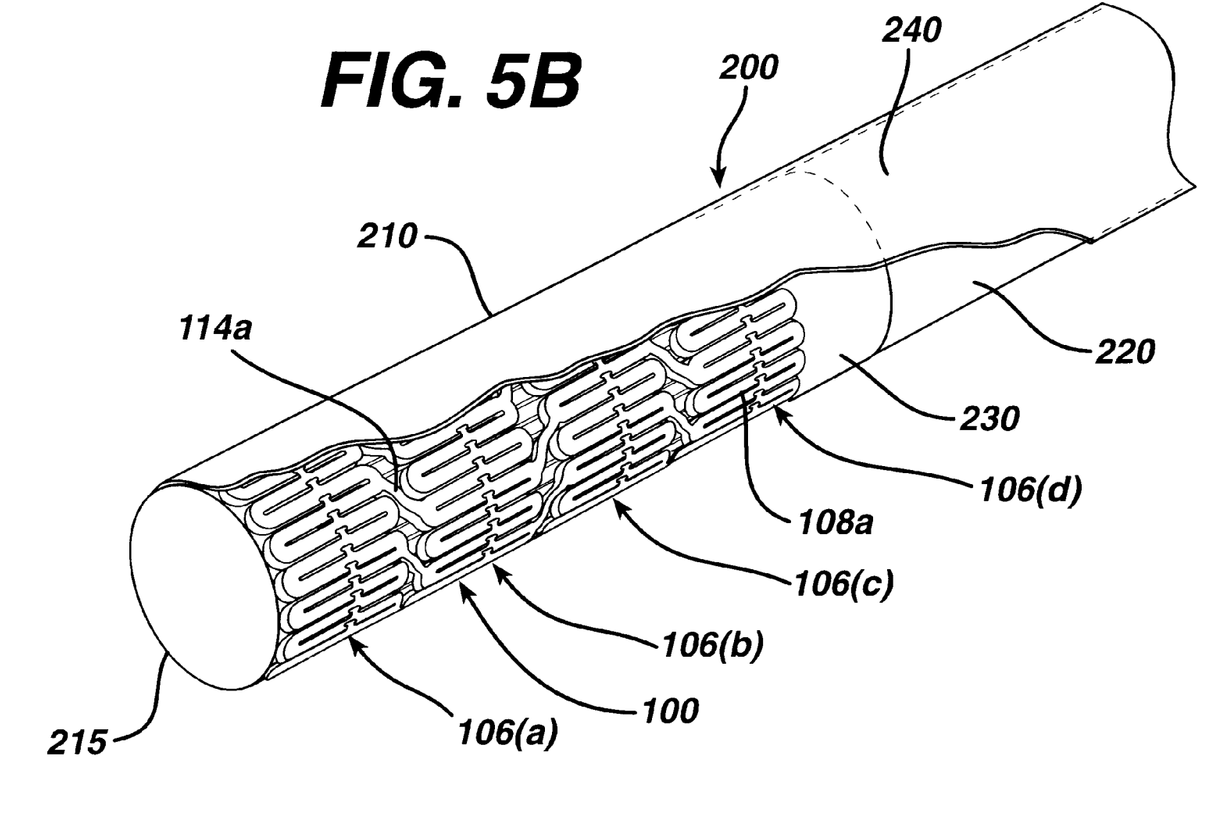
FIG. 5B is a partial perspective view of a distal end of an apparatus according to the present invention utilizing the stent of FIG. 1B.

The present invention also includes an apparatus and method for stenting a vessel utilizing the stent 100 (both the interlocking bridge 114 embodiment and the interlocking strut 108a embodiment). The stenting apparatus according to the present invention is generally designated 200 as best shown in FIGS. 5A and 5B. FIG. 5A illustrates the apparatus 200 (as a catheter) which includes the stent 100 (the interlock bridge 114 embodiment) and FIG. 5B illustrates the apparatus 200 including the second embodiment for the stent 100 (the interlocking strut 108a embodiment). As illustrated in FIGS. 5A and 5B, the catheter 200 has a distal end 210 culminating in a distal tip 215. The catheter 200 includes an inner sleeve 220 extending to the distal tip 215. An expandable member 230, such as an inflatable balloon, is fixed to the inner sleeve 220 at the distal end 210 of the catheter 200. As is well understood in the field, the expandable member 230 is expanded, such as through inflation with a hydraulic or pneumatic fluid, and is expandable from a collapsed or closed configuration to an open or expanded configuration. The stent 100 (both embodiments of FIGS. 1A and 1B) according to the present invention are secured to the distal end of the catheter 200 by closing the stent 100 over the expandable member 230 and the inner sleeve 220 as best illustrated in FIGS. 5A and 5B. The stent 100 is secured to the catheter 200 by closing the stent 100 respectively by moving the stent 100 and to its locked configuration. As described above, the locked configuration for the stent 100 includes interlocking the bridges 114 (for the interlocking bridge embodiment FIG. 5A) and for interlocking the struts 108a (for the intrelocking strut embodiment FIG. 5B) in the respective manner described above.

In securing the stent 100 to the catheter distal end 210 for the interlocking bridge embodiment of FIG. 5A, the bridges 114 are moved and interlocked (as shown in FIG. 3A) such that the stent 100 is locked and in its closed configuration over the expandable member 230.

In securing the stent 100 to the catheter distal end 210 for the interlocking strut embodiment of FIG. 5B, the struts 108a are moved and interlocked (as shown in FIG. 3B) such that the stent 100 is locked and in its closed configuration over the expandable member 230.

For both embodiments mentioned above, the stent 100 is thereby secured to the catheter 200 until deployment is desired. An outer sheath 240, which is made of a polymer material such as polyethylene, is used as a cover for the catheter distal end 210 and serves as an additional form of protection for securing of the stent 100 (both embodiments) to the catheter distal end 210. The cover 240 is movably positioned or movably disposed from the catheter distal end 210 in order to provide both the protection as described above as well as the unimpeded deployment of the stent 100 upon positioning of the stent 100 at its desired location.

The method of utilizing the catheter 200 according to the present invention includes first identifying a location in a patient's body for deployment of the stent 100. Upon identifying the desired deployment location, the catheter 200 is inserted within a vessel in the patient's body. The catheter 200 is used to traverse the vessel until reaching the desired location wherein the distal end 210 of the catheter 200 is positioned at the desired location within the vessel. At this point, the stent 100 is deployed to its open configuration by expanding the expandable member 230 such as by inflation. If the cover 240 is utilized to further protect and secure the stent 100 to the catheter distal end 210, the cover 240 is removed from the distal end 210 prior to expansion of the expandable member 230.

Upon expanding the stent 100 to its open configuration, the expandable member 230 is then collapsed, for instance through deflation of the expandable member, whereby the catheter 200 is removed from the deployment site of the vessel and patient's body altogether.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A stent comprising:
   a lattice of interconnecting elements defining a substantially cylindrical configuration having a first open end and a second open end, the lattice having a locked configuration and an open configuration; and
   a plurality of bridges connecting the interconnecting elements, each bridge interlocking with an adjacent bridge in the locked configuration and each bridge separating from the adjacent bridge in the open configuration, each bridge having a projection and a base, the base having a projection holding section for receiving the projection from the adjacent bridge, the interconnecting elements comprising a plurality of adjacent sections, wherein the adjacent sections comprise adjacent hoops, and each hoop comprises a plurality of loops.

2. The stent according to claim 1, wherein each hoop comprises at least one strut.

3. The stent according to claim 1, wherein each bridge has lateral arms extending from the base.

4. The stent according to claim 3, wherein the projection holding section has an opening therein.

5. The stent according to claim 4, wherein an extension is connected between the base and the projection.

6. The stent according to claim 5, wherein the extension includes a neck and the projection is located at a superior position on the neck.

7. The stent according to claim 6, wherein the projection includes at least one lateral lip.

8. The stent according to claim 7, wherein the projection holding section includes at least one lateral ledge for releasable engaging the at least one lateral lip of the projection.

9. The stent according to claim 8, wherein the projection includes at least one sidewall adjacent the at least one lateral lip.

10. The stent according to claim 9, wherein the projection holding section includes at least one lateral depression adjacent the at least one lateral ledge for releasably engaging the at least one sidewall of the projection.

11. The stent according to claim 10, wherein the at least one sidewall is curved.

12. The stent according to claim 11, wherein the at least one lateral depression is curved.

13. The stent according to claim 12, wherein the lateral arms connect the interconnecting elements.

14. The stent according to claim 1, wherein the stent is made of an alloy.

15. The stent according to claim 14, wherein the stent is made of stainless steel.

16. The stent according to claim 1, wherein the stent is crush recoverable.

17. The stent according to claim 16 wherein the stent is made of nickel titanium (NiTi).

18. The stent according to claim 14, wherein the stent is made of a superelastic alloy.

19. The stent according to claim 18, wherein the stent is made of nickel titanium (NiTi).

20. A stent comprising:
    a lattice of interconnecting elements defining a substantially cylindrical configuration having a first open end and a second open end, the lattice having a locked configuration and an open configuration, the interconnecting elements including a plurality of struts, each strut interlocking with an adjacent strut in the locked configuration and each strut separating from the adjacent strut in the open configuration, and at least one bridge connected between a pair of struts, wherein each strut has a projection and a base, the base having a projection holding section for receiving the projection from the adjacent strut, and the interconnecting elements comprising a plurality of adjacent sections, the adjacent sections comprising adjacent hoops, each hoop comprising a plurality of loops.

21. The stent according to claim 20, wherein each hoop comprises at least one strut.

22. The stent according to claim 20, wherein each strut has lateral arms extending from the base.

23. The stent according to claim 22, wherein the projection holding section has an opening therein.

24. The stent according to claim 23, wherein an extension is connected between the base and the projection.

25. The stent according to claim 24, wherein the projection includes at least one lateral lip.

26. The stent according to claim 25, wherein the projection holding section includes at least one lateral ledge for releasable engaging the at least one lateral lip of the projection.

27. The stent according to claim 26, wherein the projection includes at least one sidewall adjacent the at least one lateral lip.

28. The stent according to claim 27, wherein the projection holding section includes at least one lateral depression adjacent the at least one lateral ledge for releasable engaging the at least one sidewall of the projection.

29. The stent according to claim 28, wherein the at least one sidewall is curved.

30. The stent according to claim 29, wherein the at least one depression is curved.

31. The stent according to claim 20, wherein the stent is made of an alloy.

32. The stent according to claim 31, wherein the stent is made of stainless steel.

33. The stent according to claim 20, wherein the stent is crush recoverable.

34. The stent according to claim 33 wherein the stent is made of nickel titanium (NiTi).

35. The stent according to claim 31, wherein the stent is made of a superelastic alloy.

36. The stent according to claim 35, wherein the stent is made of nickel titanium (NiTi).

* * * * *